US 8,738,957 B2

(12) United States Patent
Fehr et al.

(10) Patent No.: US 8,738,957 B2
(45) Date of Patent: *May 27, 2014

(54) APPARATUS AND METHOD FOR PROCESSING A WIRELESSLY RECEIVED INFORMATION ENCODED IN FORM OF EMBEDDED DATA AND CLOCK

(75) Inventors: Jean-Noel Fehr, Neuenburg (CH); Thomas Von Buren, Bern (CH); Urs Anliker, Gumligen (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/364,546

(22) Filed: Feb. 2, 2012

(65) Prior Publication Data
US 2012/0166858 A1  Jun. 28, 2012

Related U.S. Application Data

(62) Division of application No. 12/134,944, filed on Jun. 6, 2008, now Pat. No. 8,132,037.

(51) Int. Cl.
*G06F 1/00* (2006.01)
*G06F 19/00* (2011.01)

(52) U.S. Cl.
CPC ........ *G06F 19/3418* (2013.01); *G06F 19/3456* (2013.01); *G06F 19/3481* (2013.01); *G06F 19/30* (2013.01); *G06F 19/327* (2013.01)
USPC .................................................... 713/500

(58) Field of Classification Search
CPC ............ G06F 19/3418; G06F 19/3456; G06F 19/3481; G06F 19/30; G06F 19/327
USPC ......................................................... 713/500
See application file for complete search history.

(56) References Cited

U.S. PATENT DOCUMENTS 3,654,492 A  4/1972  Clark
4,493,021 A  1/1985  Agrawal et al.
(Continued)

FOREIGN PATENT DOCUMENTS

EP  1109586 A2  6/2001
EP  1347705 A2  1/2003
(Continued)

OTHER PUBLICATIONS

Paradigm Pump Manual, User Guide, 2006, Medtronic MiniMed (176 pages).

*Primary Examiner* — Thomas Lee
*Assistant Examiner* — Xuxing Chen
(74) *Attorney, Agent, or Firm* — Roche Diagnostics Operations, Inc.

(57) ABSTRACT

An electronic device (12) for processing information that includes data and clock information and that is wirelessly received from another electronic device (14) may include a first processor (18) that controls only wireless communications with the another electronic device (14) and excluding operations associated only with the electronic device (12), a second processor (16) that controls the operations associated only with the electronic device (12) and excluding the wireless communications with the another device (14), and means (30-30'''') for extracting the clock information and the data from the wirelessly received information and providing a corresponding clock signal and the data to the second processor (16) for synchronous receipt of the data by the second processor (16) using the clock signal.

11 Claims, 5 Drawing Sheets

(56) References Cited

U.S. PATENT DOCUMENTS

| | | | |
|---|---|---|---|
| 5,582,593 | A | 12/1996 | Hultman |
| 5,665,065 | A | 9/1997 | Colman et al. |
| 5,726,650 | A * | 3/1998 | Yeoh et al. .................... 341/70 |
| 5,907,797 | A | 5/1999 | Hanatatsu et al. |
| 5,925,021 | A | 7/1999 | Castellano et al. |
| 6,427,088 | B1 | 7/2002 | Bowman, IV et al. |
| 6,540,672 | B1 | 4/2003 | Simonsen et al. |
| 6,551,276 | B1 | 4/2003 | Mann et al. |
| 6,554,798 | B1 | 4/2003 | Mann et al. |
| 6,562,001 | B2 | 5/2003 | Lebel et al. |
| 6,564,105 | B2 | 5/2003 | Starkweather et al. |
| 6,571,128 | B2 | 5/2003 | Lebel et al. |
| 6,577,899 | B2 | 6/2003 | Lebel et al. |
| 6,585,644 | B2 | 7/2003 | Lebel et al. |
| 6,634,014 | B1 | 10/2003 | Lindberg et al. |
| 6,648,821 | B2 | 11/2003 | Lebel et al. |
| 6,650,951 | B1 | 11/2003 | Jones et al. |
| 6,659,948 | B2 | 12/2003 | Lebel et al. |
| 6,668,196 | B1 | 12/2003 | Villegas et al. |
| 6,687,546 | B2 | 2/2004 | Lebel et al. |
| 6,694,191 | B2 | 2/2004 | Starkweather et al. |
| 6,733,446 | B2 | 5/2004 | Lebel et al. |
| 6,738,670 | B1 | 5/2004 | Almendinger et al. |
| 6,740,075 | B2 | 5/2004 | Lebel et al. |
| 6,744,350 | B2 | 6/2004 | Blomquist |
| 6,758,810 | B2 | 7/2004 | Lebel et al. |
| 6,768,425 | B2 | 7/2004 | Flaherty et al. |
| 6,810,290 | B2 | 10/2004 | Lebel et al. |
| 6,811,533 | B2 | 11/2004 | Lebel et al. |
| 6,811,534 | B2 | 11/2004 | Bowman, IV et al. |
| 6,813,519 | B2 | 11/2004 | Lebel et al. |
| 6,872,200 | B2 | 3/2005 | Mann et al. |
| 6,873,268 | B2 | 3/2005 | Lebel et al. |
| 6,936,029 | B2 | 8/2005 | Mann et al. |
| 6,950,708 | B2 | 9/2005 | Bowman IV et al. |
| 6,958,705 | B2 | 10/2005 | Lebel et al. |
| 6,974,437 | B2 | 12/2005 | Lebel et al. |
| 6,979,326 | B2 | 12/2005 | Mann et al. |
| 6,997,920 | B2 | 2/2006 | Mann et al. |
| 7,024,245 | B2 | 4/2006 | Lebel et al. |
| 7,109,878 | B2 | 9/2006 | Mann et al. |
| 7,171,274 | B2 | 1/2007 | Starkweather et al. |
| 7,179,226 | B2 | 2/2007 | Crothall et al. |
| 7,204,823 | B2 | 4/2007 | Estes et al. |
| 7,278,983 | B2 | 10/2007 | Ireland et al. |
| 7,347,819 | B2 | 3/2008 | Lebel et al. |
| 7,369,635 | B2 | 5/2008 | Spital et al. |
| 7,454,644 | B2 * | 11/2008 | Giovinazzi et al. ........... 713/500 |
| 2003/0065308 | A1 | 4/2003 | Lebel |
| 2003/0065536 | A1 | 4/2003 | Hansen |
| 2003/0110512 | A1 * | 6/2003 | Maari .......................... 725/131 |
| 2003/0163088 | A1 | 8/2003 | Blomquist |
| 2003/0176933 | A1 | 9/2003 | Lebel |
| 2003/0212364 | A1 | 11/2003 | Mann et al. |
| 2003/0212441 | A1 | 11/2003 | Starkweather et al. |
| 2004/0044272 | A1 | 3/2004 | Moerman et al. |
| 2004/0068230 | A1 | 4/2004 | Estes et al. |
| 2004/0193090 | A1 | 9/2004 | Lebel et al. |
| 2004/0225338 | A1 | 11/2004 | Lebel et al. |
| 2004/0235446 | A1 | 11/2004 | Faherty et al. |
| 2004/0260233 | A1 | 12/2004 | Garibotto et al. |
| 2004/0266423 | A1 * | 12/2004 | Morikawa et al. ............ 455/424 |
| 2005/0003470 | A1 | 1/2005 | Nelson et al. |
| 2005/0009126 | A1 | 1/2005 | Andrews et al. |
| 2005/0010269 | A1 | 1/2005 | Lebel et al. |
| 2005/0022274 | A1 | 1/2005 | Campbell et al. |
| 2005/0065464 | A1 | 3/2005 | Talbot et al. |
| 2005/0090808 | A1 | 4/2005 | Malave et al. |
| 2005/0171513 | A1 | 8/2005 | Mann et al. |
| 2005/0215982 | A1 | 9/2005 | Malave et al. |
| 2005/0255843 | A1 * | 11/2005 | Hilpisch et al. ............... 455/425 |
| 2006/0132292 | A1 | 6/2006 | Blomquist |
| 2006/0173444 | A1 | 8/2006 | Choy |
| 2006/0198364 | A1 * | 9/2006 | Fujii ............................. 370/352 |
| 2006/0281454 | A1 | 12/2006 | Gray |
| 2007/0006181 | A1 | 1/2007 | Zimman et al. |
| 2007/0014374 | A1 * | 1/2007 | Hershbarger ................. 375/258 |
| 2007/0060869 | A1 | 3/2007 | Tolle |
| 2007/0060870 | A1 | 3/2007 | Tolle |
| 2007/0060871 | A1 | 3/2007 | Istoc |
| 2007/0153705 | A1 | 7/2007 | Rosar |
| 2008/0033357 | A1 | 2/2008 | Mann |
| 2008/0175344 | A1 * | 7/2008 | Menolfi et al. ................ 375/376 |
| 2010/0068998 | A1 * | 3/2010 | Zyambo et al. ............... 455/41.1 |
| 2010/0134158 | A1 | 6/2010 | Pignol et al. |

FOREIGN PATENT DOCUMENTS

| | | |
|---|---|---|
| EP | 0830160 B1 | 3/2003 |
| EP | 1423046 A2 | 6/2004 |
| EP | 1473050 A1 | 11/2004 |
| EP | 1611834 A2 | 1/2006 |
| EP | 1135056 B1 | 8/2006 |
| EP | 1759726 A2 | 3/2007 |
| GB | 2389419 A | 6/2002 |
| WO | 0228454 A2 | 4/2002 |
| WO | 03005278 A1 | 1/2003 |
| WO | 03009207 A1 | 1/2003 |
| WO | 03009208 A1 | 1/2003 |
| WO | 03015838 A2 | 2/2003 |
| WO | 2004008956 A2 | 1/2004 |
| WO | 2004098390 A2 | 11/2004 |
| WO | 2007021892 A1 | 2/2007 |
| WO | 2007021894 A2 | 2/2007 |
| WO | 2008097316 A1 | 8/2008 |

* cited by examiner

APPARATUS AND METHOD FOR PROCESSING A WIRELESSLY RECEIVED INFORMATION ENCODED IN FORM OF EMBEDDED DATA AND CLOCK

CROSS-REFERENCE TO RELATED U.S. APPLICATION

This is a divisional of U.S. application Ser. No. 12/134,944, filed Jun. 6, 2008, now U.S. Pat. No. 8,132,037 the disclosure of which is incorporated herein by reference in its entirety.

FIELD OF THE INVENTION

The present invention relates generally to electronic devices configured to wirelessly communicate with other electronic devices, and more specifically to processing wirelessly communicated data and clock information within either or both of the electronic devices.

BACKGROUND

It is generally known to provide for wireless communications between two electronic devices such as a medical device, e.g., an ambulatory medical device, and a remote electronic device. It is desirable with such arrangements to separate the control of telemetry operations from device function operations within either or both of the wirelessly communicating devices.

SUMMARY

The present invention may comprise one or more of the features recited in the attached claims, and/or one or more of the following features and combinations thereof. An electronic device for processing information that includes data and clock information and that is wirelessly received from another electronic device may comprise a first processor that controls only wireless communications with the another electronic device and excluding operations associated only with the electronic device, a second processor that controls the operations associated only with the electronic device and excluding the wireless communications with the another device, and means for extracting the clock information and the data from the wirelessly received information and providing a corresponding clock signal and the data to the second processor for synchronous receipt of the data by the second processor using the clock signal.

In one embodiment, the means for extracting the clock information and the data from the wirelessly received information may comprise a phase lock loop circuit having an input connected to the first processor, a first output connected to the second processor and a second output, and a decoder circuit having a first input connected to the first processor, a second input connected to the second output of the phase lock loop circuit and an output connected to the second processor. The first processor may provide the wirelessly received information to the inputs of the phase lock loop circuit and the decoder circuit. The phase lock loop circuit may extract the clock information from the wirelessly received information and produce the clock signal. The decoder circuit may decode the data from the wirelessly received information.

The wirelessly received information may further comprise a preamble. The phase lock loop circuit may be configured to be responsive to the preamble to lock and run with a phase lock loop clock that operates at a phase lock loop clock rate. The decoder circuit may receive the phase lock loop clock via the second input thereof. The decoder circuit may be configured to decode the data from the wirelessly received information by removing the clock information from the wirelessly received information as a function of the phase lock loop clock. The phase lock loop circuit may be configured to be responsive to the transitions of the data contained in the wirelessly received information to update operation of the phase lock loop circuit.

In an alternative embodiment, the means for extracting the clock information and the data from the wirelessly received information may comprise a phase lock loop circuit having an input connected to the first processor and an output connected to the second processor. The first processor may provide the wirelessly received information to the input of the phase lock loop circuit. The phase lock loop circuit may extract the clock information from the wirelessly received information and produces the clock signal. The second processor may include a memory having instructions stored therein that are executable by the second control circuit to decode the data from the wirelessly received information at a decode rate defined by the clock signal. The wirelessly received information may further comprise a preamble. The phase lock loop circuit may be configured to be responsive to the preamble to lock and run with a phase lock loop clock that operates at a phase lock loop clock rate. Operation of the phase lock loop circuit may be updated by transitions of the data contained in the wirelessly received information.

In another alternate embodiment, the second processor may include a memory and the means for extracting the clock information and the data from the wirelessly received information may comprise instructions stored in the memory that are executable by the second processor to extract the clock information from the wirelessly received information to produce the clock signal and to decode the data from the wirelessly received information at a decode rate defined by the clock signal.

In a further alternative embodiment, the wirelessly received information may be received by the first processor in two separate channels in which a first channel contains the data and a second channel contains the clock information. In this embodiment, the means for extracting the clock information and the data from the wirelessly received information may comprise means for processing the first channel to extract the data and means for processing the second channel to extract the clock signal from the clock information. The first processor may be configured to wirelessly receive information from the another electronic device according to a predefined communication protocol in which the first channel is an audio channel and in which the second channel is a data channel.

DESCRIPTION OF THE ILLUSTRATIVE EMBODIMENTS

For the purposes of promoting an understanding of the principles of the invention, reference will now be made to a number of illustrative embodiments shown in the attached drawings and specific language will be used to describe the same.

Figure 1:
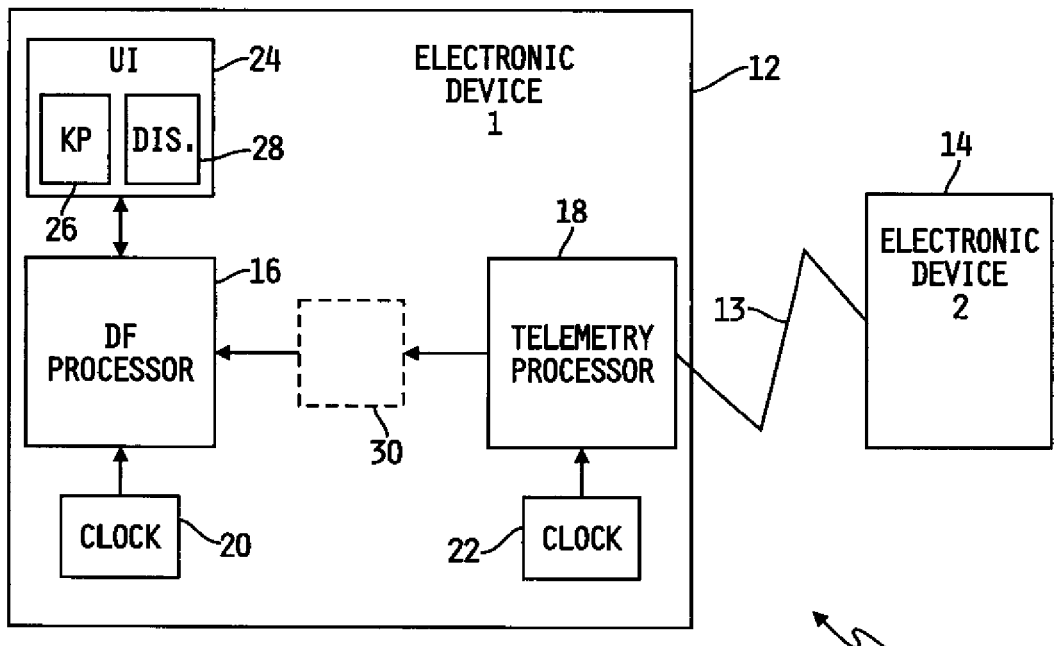
FIG. 1 is a diagram of one illustrative embodiment of a wireless communication system configured for wireless data and clock communications between two separate electronic devices.

Referring now to FIG. 1, one illustrative embodiment of a wireless communication system 10 is shown that is configured for wireless communications between two separate electronic devices 12 and 14. In one illustrative embodiment, the electronic device 12 is a medical device and the electronic device 14 is a remote electronic device. In this embodiment, the medical device 12 may be, for example, an ambulatory medical device, although the medical device 12 may alternatively be or include a non-ambulatory medical device. Examples of such an ambulatory medical device may include, but should not be limited to, one or any combination of a medication or drug delivery device such as an infusion pump, a glucose meter, a body fluid analyte sensor system including one or more subcutaneous and/or implanted body fluid analyte sensors, a remote terminal representing a remote infusion pump display on which data from the infusion pump is displayed to a user, or the like. The remote electronic device 14, in this embodiment, may be or include, but should not be limited to, a conventional personal data assistant (PDA) device, an application-specific remote electronic device that may be hand-held, attachable or mountable to clothing, configured to be worn by a person such as on or about a limb or portion thereof, on or about a head or portion thereof, or on or about a body or portion thereof, attachable to a key ring, or the like, a portable wireless communication device with an on-board glucose meter, a smart phone, a personal computer (PC), a laptop, notebook or similar computer, or the like. In one specific embodiment, which should not be considered to be limiting in any way, the electronic device 12 is an insulin infusion pump and the remote electronic device 14 is a handheld smart phone. In other embodiments, the functionality of the electronic devices 12 and 14 may be reversed, i.e., the electronic device 14 may be a medical device, ambulatory or otherwise, and the electronic device 12 may be a remote electronic device. In still other embodiments, the electronic devices 12 and 14 may both be medical devices, ambulatory or otherwise, and in further embodiments the electronic devices 12 and 14 may both be non-medical electronic devices.

The electronic device 14 may or may not be configured identically to the electronic device 12, and in any case the electronic devices 12 and 14 are configured to communicate wirelessly with each other via a conventional communication medium 13. Examples of the communication medium 13 may include, but should not be limited to, radio frequency (RF), infrared (IR), microwave, inductive coupling, or the like. In one specific example, which should not be considered limiting in any way, the electronic devices 12 and 14 are each configured to communicate via RF according to a conventional BlueTooth® radio frequency communications protocol.

In the illustrated embodiment, the electronic device 12 includes a device function processor 16 that is configured to control all functional operations of the device 12 but not including telemetry operations, i.e., wireless communications with the electronic device 14. A clock circuit, 20 is electrically connected to the device function processor 16, and the timing of operation of the device function processor 16 is controlled by the clock circuit 20. The electronic device 12 further includes a telemetry processor 18 that is electrically coupled to the device function processor 16. The telemetry processor 18 is configured to control wireless communication with the electronic device 14, but not device functions, i.e., non-telemetry operations of the electronic device 12. Another clock circuit 22 is electrically connected to the telemetry processor 18, and the timing of operation of the telemetry processor 18 is controlled by the clock circuit 22.

A clock and data decoding circuit 30 is illustratively connected between the device function processor 16 and the telemetry processor 18. The clock and data decoding circuit 30 is shown in FIG. 1 as a dashed line representation to indicate that in some embodiments all of the clock and data decoding circuitry is outside of and between the device function processor 16 and the telemetry processor 18, in other embodiments some or all of the clock and data decoding circuitry 30 may be located in the device function processor 16, and in still other embodiments some or all of the clock and data decoding circuitry 30 may be located in the telemetry processor 18. In any case, the clock and data decoding circuit 30 is configured to decode and separate clock signals and data signals from wireless messages sent by the electronic device 14 to the electronic device 12 via the communication medium 13, and to use the decoded clock signals to control transfer of the decoded data signals from the telemetry processor 18 to the device function processor 16.

The electronic device 12 further includes a user interface 24 that is electrically connected to the device function processor 16. The user interface 24 illustrated in FIG. 1 illustratively includes a conventional key pad 26 and a conventional display unit 28. The device function processor 16 illustratively receives user input via the key pad 26, and provides notifications or messages to the user via the display unit 28. The key pad 26 may be or include one or more special purpose keys or buttons, a conventional full-function key board such as those typically found on a personal, laptop or notebook computer, or some number of keys or buttons between one key or button and a full-function key board. The display unit 28 may be a conventional liquid crystal display (LCD) unit, or may alternatively be or include a conventional vacuum fluorescent display unit, a conventional light emitting diode (LED) display, one or more conventional light emitting diodes or segments, or the like. Alternatively or additionally, the user interface 24 may include one or more additional information input devices for providing information from a user or another electronic system to the electronic device 12. Examples of such one or more additional information input devices include, but should not be limited to, a conventional touch-screen display, conventional voice-activated information input circuitry, a conventional wired or wireless data port configured to communicate with an external electronic system or the like. Alternatively or additionally still, the user interface 24 may include one or more other notification or information transfer devices for providing information to a user or other electronic system. Examples of such one or more other notification or information transfer devices include, but should not be limited to, a conventional audio indication device, one or more conventional speakers, a conventional tactile indication device, a conventional wired or wireless data port configured to communicate with an external electronic system or the like.

Figure 2:
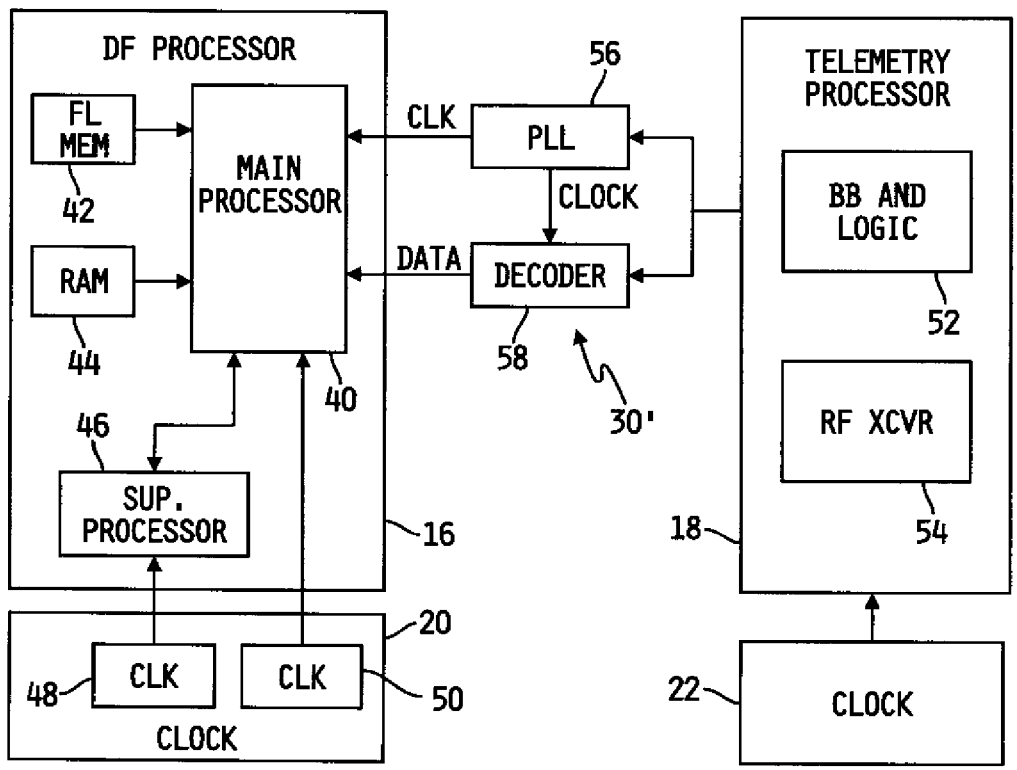
FIG. 2 is a diagram of one illustrative embodiment of the device function module and the telemetry module of FIG. 1 that further includes a clock and data decoding circuit disposed between the two modules.

Referring now to FIG. 2, a diagram of one illustrative embodiment of the device function processor 16, the telemetry processor 18 and the clock and data decoding circuit 30' respectively is shown. In the illustrated embodiment, the device function processor 16 includes two separate processor circuits. A main processor 40 is electrically connected to a non-volatile memory 42, e.g., a conventional FLASH memory, a volatile memory 44, e.g., a random access memory (RAM) and a clock circuit 50. The main processor 40 may be, for example, a model V850SA1, 32-bit microcontroller that is commercially available from NEC corporation, although the main processor 40 may alternatively be implemented using other conventional microprocessor-based or non-microprocessor-based circuits.

The device function processor 16 further includes a supervisor processor 46 that is electrically connected to the main processor 40 and also to a clock circuit 48. The clock circuits 48 and 50 illustratively comprise the clock circuit 20 illustrated in FIG. 1. The supervisor processor 46 may be, for example, a model PIC12C509, 8-bit microcontroller that is commercially available from Microchip Technology, Inc., although the supervisor processor 46 may alternatively be implemented using other conventional microprocessor-based or non-microprocessor-based circuits. Generally, the main processor 40 controls the functional operations of the electronic device 12 and the supervisor processor 46 continually monitors the main processor 40 and activates an alarm if the main processor 40 malfunctions.

In the illustrated embodiment, the telemetry processor 18 is electrically connected to the clock circuit 22, and includes a conventional base band and logic section 52 and a conventional radio frequency (RF) transceiver circuit 54. In one embodiment, the telemetry processor 18 includes a main processor and a separate wireless communication processor. In one example of this embodiment in which the wireless communication protocol is a BlueTooth® RF communications protocol, the wireless communication processor may, for example, be a BlueCore 4-ROM Plug-N-Go, single chip radio and baseband circuit that is commercially available from a number of suppliers such as CSR, and the main processor may be, for example, a model MSP430F2471 16-bit microcontroller as described above. In this example embodiment, the wireless communication processor handles the BlueTooth® communications, i.e., the lower layer of the BlueTooth® protocol stack, and the main processor handles the upper layer of the BlueTooth® protocol stack and, in some embodiments, an additional security layer. In alternative embodiments, the main processor and the wireless communication processor may be substituted by a single telemetry processor, e.g., a single BlueCore 4-ROM Plug-N-Go, single chip radio and baseband circuit.

The electronic device 14 controls all communication on the electronic device 12 between the device function processor 16 and the telemetry processor 18. In particular, the electronic device 14 generates a clock signal which is passed wirelessly along with data in the form of messages to the electronic device 12 via the wireless communication medium 13. The electronic device 12 demodulates the clock signal from the wireless messages, and the clock signal is then employed within the electronic device 12 to control the timing of communication of the data between the device function processor 16 and the telemetry processor 18. All communication between the device function processor 16 and the telemetry processor 18 is thus controlled by messages wirelessly transmitted by the electronic device 14 and received by the electronic device 12. The electronic device 14 may send polling requests, interrupts, triggers, synchronization and the like to the device function processor 16 via the telemetry processor 18.

During communications between the device function processor 16 and the telemetry processor 18 as just described, the device function processor 16 and the telemetry processor 18 operate separately and independently of each other. The device function processor 16 controls only the functions and operations of the electronic device 12 that are not telemetry related, and the telemetry processor 18 controls only the telemetry operations. No signals related to polling requests, interrupts, triggers, synchronization or the like are originated by and sent from the device function processor 16 to the telemetry processor 18 or vice versa. Moreover, the device function processor 16 does not control any aspect of when or how the telemetry processor 18 transmits or receives messages or information packets, and the telemetry processor 18 does not control any aspect of when or how the device function processor 16 processes messages or information packets. Any message or information packet that is wirelessly transmitted by the electronic device 14 to the electronic device 12 is forwarded unchanged by the telemetry processor 18 to the device function processor 16.

In one embodiment, the electronic device 14 wirelessly transmits data and clock signals to the electronic device 12 using self-clocking codes. Generally, self-clocking codes combine data and a clock signal into one signal such that the coded signal can be decoded to determine the data and clock signal without a separate clock or other source of synchronization. This is typically accomplished by including synchronization information within the data portion of the message. For example, the clock signal may typically be included as some type of run length limited code (e.g., one that limits the number of back-to-back ones or zeros), and the run length limit is generally selected to limit the run length of ones or zeros in such a way that the receiver of the message can maintain synchronization for the duration of the message. It will be understood, however, that the inclusion of clock signal information in wireless messages transmitted from the electronic device 14 to the electronic device 12 will generally increase the signal bandwidth over messages transmitted without embedded clock signals.

Generally, including self-clocking codes in the wireless signals transmitted by the electronic device 14 to the electronic device 12 requires suitable circuitry or software for decoding the clock and data signals from the wireless messages. In the embodiment illustrated in FIG. 2, for example, such a clock and data decoding circuit 30' is provided separately from the device function processor 16 and the telemetry processor 18. In the illustrated embodiment, the clock and data decoding circuit 30' includes a conventional phase lock loop (PLL) 56 and a decoder circuit 58 each having an input electrically connected to and receiving information packets from the telemetry processor 18. The telemetry processor 18 is operable to receive messages wirelessly transmitted by the electronic device 14, and to extract the information packets from the wirelessly received messages by unpacking the information packets from the wireless communication protocol, e.g., from the BlueTooth® communication protocol. In the illustrated embodiment, the information packets include data and clock information in the form of self-clocking codes that are decoded by the PLL 56 and the decoder circuit 58. The PLL 56 is operable to extract the clock information from the information packets to produce clock signals, and to provide a PLL clock to the decoder circuit 58 as illustrated in FIG. 2. The decoder circuit 58 is operable to decode the data from the information packets by removing the self-clocking codes embedded in the information packets using the PLL clock. Outputs of the PLL 56 and the decoder circuit 58 are electrically connected to the device function processor 16, and the resulting clock signal output of the PLL 56 and the decoded data signal output of the decoder circuit 58 are both provided to the main processor 40 of the device function processor 16. The main processor 40 then uses the clock signal provided by the PLL 56 to read the data signal provided by the decoder circuit 58. The communication between the telemetry processor 18 and the device function processor 16 is thus synchronized by the clock signal generated and provided by the electronic device 14.

Figure 3:
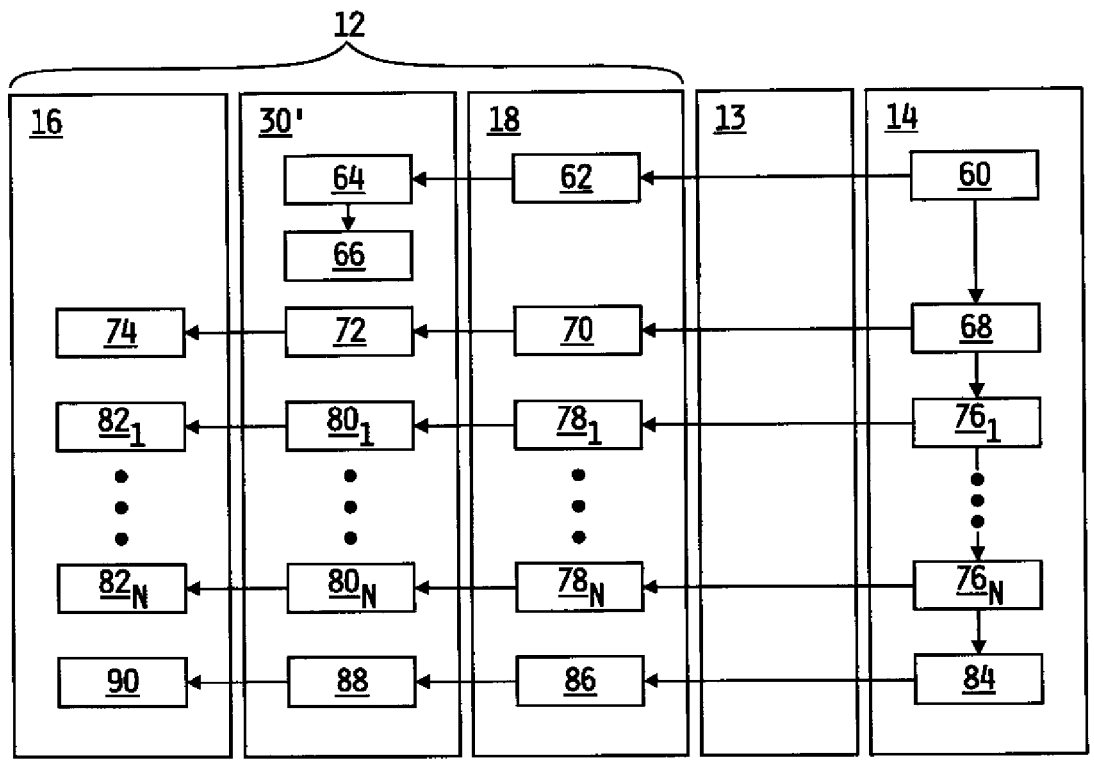
FIG. 3 is a flowchart of one illustrative embodiment of a process for transmitting data from one electronic device in the form of wireless messages containing self-clocking codes to the device function processor of the other electronic device using the clock and data decoding circuit illustrated in FIG. 2.

Referring now to FIG. 3, a flowchart is shown of one illustrative embodiment of a process for transmitting data from the electronic device 14 in the form of wireless messages containing self-clocking codes to the device function processor 16 of the electronic device 12 using the clock and data decoding circuit 30' illustrated in FIG. 2. The flowchart of FIG. 3 is partitioned into the various entities and device/electrical components that carry out the various acts of the clock and data extracting process. Thus, for example, the device function processor 16 will carry out some of the acts, the clock and data decoding circuit 30' will carry out some of the acts, the telemetry processor 18 will carry out some of the acts, and the electronic device 14 will carry out some of the acts. The illustrated process begins at step 60 where the electronic device 14 wirelessly transmits a preamble to the telemetry processor 18 of the electronic device 12 via the wireless communication medium 13. Thereafter at step 62, the telemetry processor 18 is operable to unpack the preamble from the wireless communication protocol structure and to provide the unpacked preamble to the clock and data decoding circuit 30' to wake up the communication channel between the telemetry processor 18 and the device function processor 16 at step 64. Thereafter at step 66, the information contained in the unpacked preamble locks the PLL 56 such that the PLL runs with the PLL clock operating at a predetermined PLL clock rate or frequency. In one embodiment, the preamble contains a sequence of ones and zeros that changes state at each bit, e.g., 10101010, although this disclosure contemplates other preamble contents. With the PLL 56 running at a PLL clock rate, the electronic device 14 then wirelessly transmits a start command with embedded self-clocking codes at step 68 to the telemetry processor 18 of the electronic device 12 via the wireless communication medium 13. The telemetry processor 18 is thereafter operable at step 70 to unpack the start command from the wireless communication protocol structure, and to provide the unpacked start command to the clock and data decoding circuit 30'. At step 72, the decoder circuit 58 decodes the unpacked start command by removing the self-clocking codes from the unpacked start command using the PLL clock provided by the PLL 56. The resulting decoded start command is sent to the device function processor 16 at step 74. While the decoded start command is being sent to the device function processor 16, the PLL clock is updated at each high to low or low to high transition of the data transmission. When the decoded start command is received by the device function processor 16, the device function processor 16 is prepared to receive data until a stop command is received.

After sending the start command, the electronic device 14 is operable to wirelessly transmit a first information packet with embedded self-clocking codes at step $76_1$. The telemetry processor 18 is thereafter operable at step $78_1$ to unpack the first information packet from the wireless communication protocol structure, and to provide the unpacked first information packet to the clock and data decoding circuit 30'. Thereafter at step $80_1$, the decoder circuit 58 decodes the unpacked information packet by removing the self-clocking codes from the unpacked first information packet using the PLL clock provided by the PLL 56. The resulting decoded first information packet is then sent to the device function processor 16 at step $82_1$. While the decoded first information packet is being sent to the device function processor 16, operation of the PLL 56 is updated at each high to low or low to high transition of the data transmission, e.g., by updating the PLL clock. When the decoded information packet is received by the device function processor 16, the device function processor 16 is acts upon the information contained in the first information packet as appropriate. This process is repeated for N information packets as illustrated in FIG. 3, where N may be any positive integer. After the last, e.g., Nth, information packet is sent, the electronic device 14 is operable at step 84 to wirelessly transmit a stop command with embedded self-clocking codes to the telemetry processor 18 of the electronic device 12 via the wireless communication medium 13. The telemetry processor 18 is thereafter operable at step 86 to unpack the stop command from the wireless communication protocol structure, and to provide the unpacked start command to the clock and data decoding circuit 30'. At step 88, the decoder circuit 58 decodes the unpacked stop command by removing the self-clocking codes from the unpacked stop command using the PLL clock provided by the PLL 56. The resulting decoded stop command is sent to the device function processor 16 at step 90. While the decoded stop command is being sent to the device function processor 16, the PLL clock is updated at each high to low or low to high transition of the data transmission. When the decoded stop command is received by the device function processor 16, the device function processor 16 is informed that no further information packets will follow until another start command is received. When the PLL 56 thereafter loses its synchronization resulting from the absence of information packets supplied to the clock and data decoding circuit 30' by the telemetry processor 18, the communication channel between the telemetry processor 18 and the device function processor 16 goes back to a sleep state.

Figure 4:
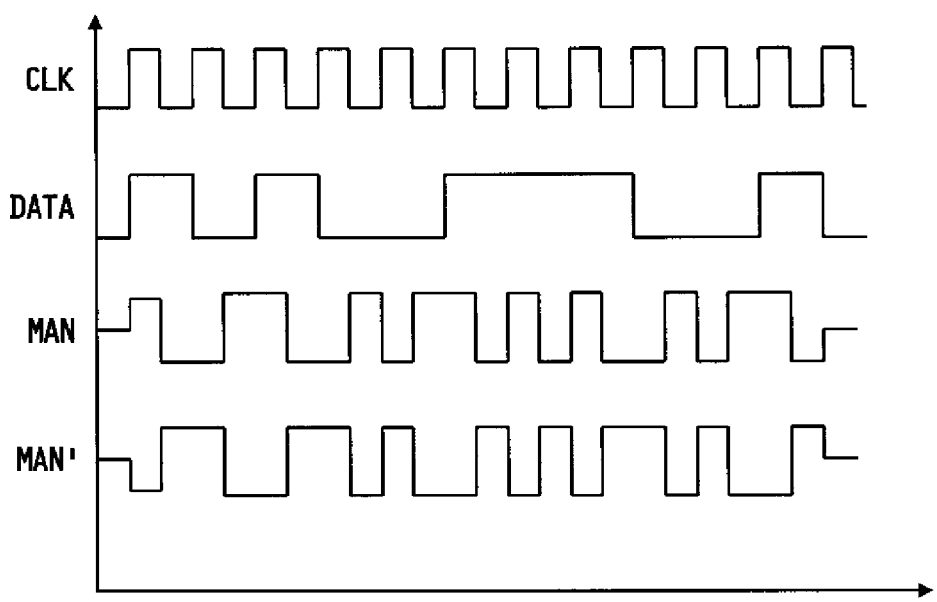
FIG. 4 is a timing diagram illustrating operation of one embodiment of the decoder circuit of FIG. 2.

Referring now to FIG. 4, a timing diagram is shown illustrating operation of one illustrative embodiment of the decoding circuit 58. In the illustrated embodiment, the clock signal exiting the PLL 56 and the data signal exiting the decoder circuit 58 are shown along with one illustrative set of decoding signals. In the illustrated example, the decoding signals are conventional Manchester decoding signals with one being the inverse of the other. The Manchester code illustrated in FIG. 4 illustratively encodes a "0" as a low to high transition in the middle of a clock cycle and a "1" as a high to low transition. The Manchester code is accordingly well suited for the illustrated communication scheme as each bit as a resynchronization transition. In alternative embodiments, other conventional self-clocking codes and corresponding decoding schemes may be used in place of the Manchester code illustrated in FIG. 4. Examples of such alternative conventional coding and decoding schemes include, but should not be limited to, Plesiochronous Digital Hierarchy, Eight-to-Fourteen Modulation, 4B5B encoding/decoding, 8b/10b self-clocking code, High-Level Data Link Control (HDLC), Modified Frequency Modulation (MFM) or the like.

Figure 5:
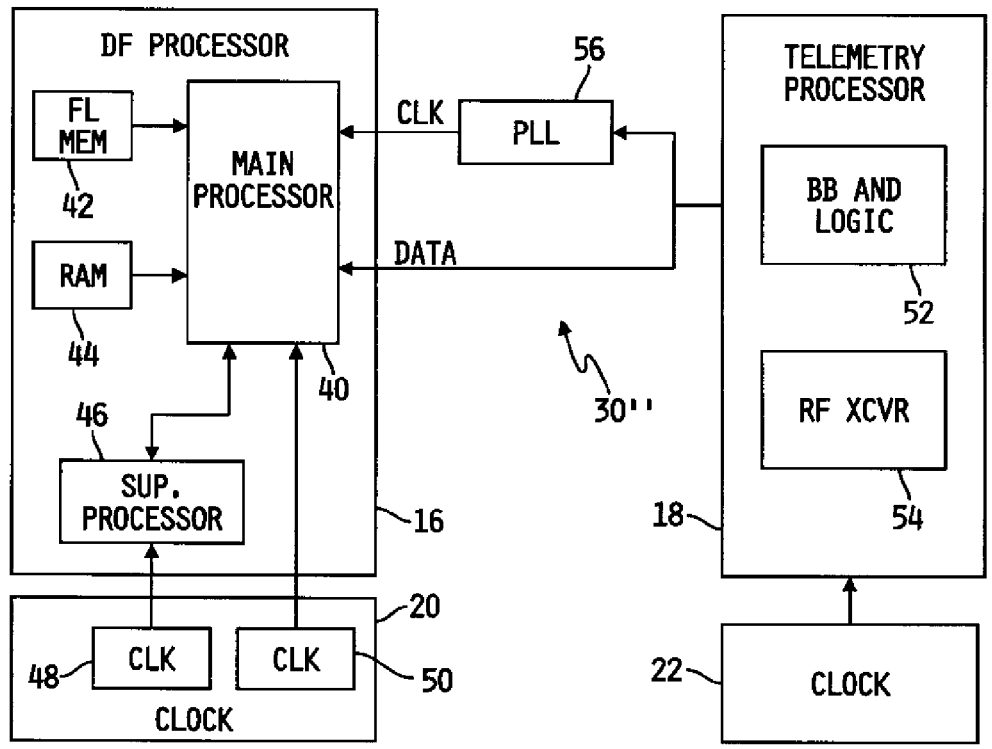
FIG. 5 is a diagram of another illustrative embodiment of the device function module and the telemetry module of FIG. 1 that includes a clock decoding circuit disposed between the two modules.
Figure 6:
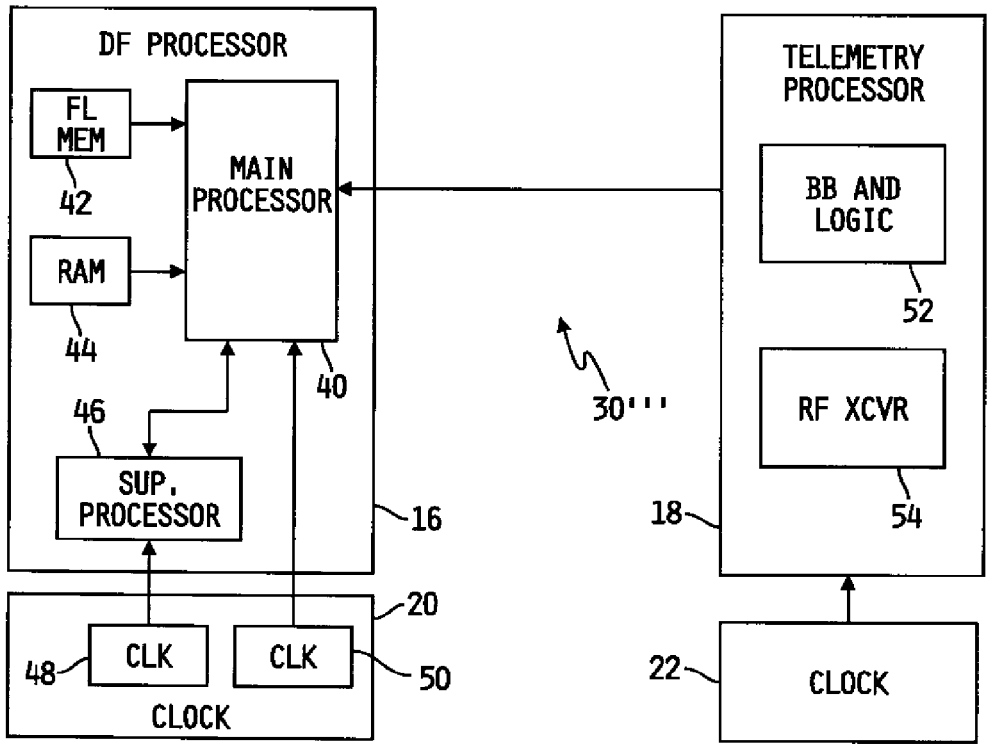
FIG. 6 is a diagram of yet another illustrative embodiment of the device function module and the telemetry module of FIG. 1 that includes a single data line connected between the two modules.

Referring now to FIG. 6, yet another illustrative embodiment of the device function processor 16, the telemetry processor 18 and the clock and data decoding circuit 30''' respectively is shown. In the illustrated embodiment, the device function processor 16 and the telemetry processor 18 are identical to the device function processor 16 and the telemetry processor 18 illustrated and describe hereinabove with respect to FIG. 2. Like numbers are therefore used in FIG. 5 to identify like components. The clock and data decoding circuit 30''' differs from the clock and data decoding circuits 30' of FIGS. 2 and 30'' of FIG. 5 in that the entirety of the clocking and data decoding circuit 30''' is, in this embodiment, included in the main processor 40 of the device function processor 16 in the form of instructions that are stored in the memory 42 and that are executable by the main processor 40 to carry out the entirety of the operation of the clock and data decoding circuit 30' as described with respect to FIGS. 2-4. For example, the instructions stored in the memory 42 are executable by the main processor 40 to extract the clock information from the wirelessly received information to produce the clock signal that was produced in the previous embodiments by the PLL 56, and to decode the data from the wirelessly received information at a decode rate defined by the clock signal. The task of the telemetry processor 18, in this embodiment, is thus to receive messages wirelessly transmitted by the electronic device 14, to unpack the messages from the wireless communication protocol structure, and to send the unpacked messages in their entirety to the device function processor 16. The PLL implementation in the main processor 40 is illustratively accomplished using software that is based on interrupts and internal timers of the main processor 40. As with the embodiment illustrated in FIG. 5, a decoding scheme other than the Manchester decoding scheme is illustratively used in this embodiment to directly convert bit codes into commands or data in the main processor 40. Again, decoding schemes based on x-to-y coding, e.g., 465B or 8610B, may illustratively be used.

Referring now to FIG. 5, another illustrative embodiment of the device function processor 16, the telemetry processor 18 and the clock and data decoding circuit 30'' respectively is shown. In the illustrated embodiment, the device function processor 16 and the telemetry processor 18 are identical to the device function processor 16 and the telemetry processor 18 illustrated and describe hereinabove with respect to FIG. 2. Like numbers are therefore used in FIG. 5 to identify like components. The clock and data decoding circuit 30'' differs from the clock and data decoding circuit 30' of FIG. 2 in that the portion of the clock and data decoding circuit 30'' that is separate from and connected between the device function processor 16 and the telemetry processor 18 includes only the PLL 56. Operation of the PLL 56 may is illustratively identical to that described above with respect to the process of FIG. 3. The decoding circuit 58, in this embodiment, is included in the main processor 40 of the device function processor 16 in the form of instructions that are stored in the memory 42 and that are executable by the main processor 40 to decode the data from the wirelessly received information at a decode rate defined by the clock signal produced by the PLL circuit 56. In this embodiment, a decoding scheme other than the Manchester decoding scheme is used to directly convert bit codes into commands or data. Illustratively, decoding schemes based on x-to-y coding, e.g., 465B or 8610B, may be used.

Figure 7:
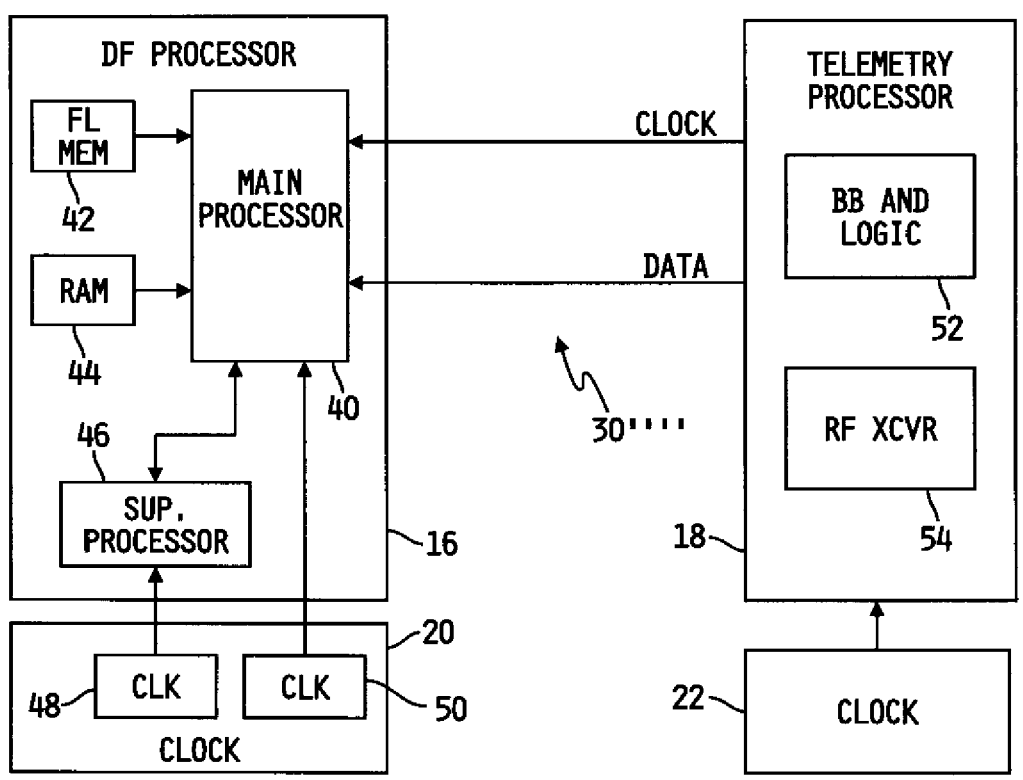
FIG. 7 is a diagram of a further illustrative embodiment of the device function module and the telemetry module of FIG. 1 that includes a clock line and a data line connected between the two modules.

Referring now to FIG. 7, yet another embodiment of the device function processor 16 and the telemetry processor 18 is shown. In the illustrated embodiment, the electronic device 14 wirelessly transmits data and clock signals to the electronic device 12 using two separate channels; one that transmits clock information and another that transmits data. The telemetry processor 18 in this embodiment is accordingly configured to process and decode the two incoming channels into two synchronous output channels; one that contains data extracted by the telemetry processor 18 from one of the two incoming channels and the other that contains a clock signal extracted by the telemetry processor 18 from the clock information in the other incoming channel. One of the synchronous output channels carries the decoded or extracted clock signal to the device function processor 16, and the other synchronous output channel carries the decoded data signal to the device function processor 16.

In one embodiment in which BlueTooth® communication protocol is used, information may be wirelessly transferred between the electronic device 12 and the electronic device 14 in the form of information packets or on a dedicated audio format (e.g., pulse code modulated) via a synchronous connection-oriented link (SCO) or an asynchronous connectionless link (ACL). Illustratively, clock and data decoding circuit 30''' in this embodiment includes a microcontroller connected to the BlueTooth® processor to extract bit streams of data from the information packets in the data channel. The audio channel may then be used to transmit a modulated audio signal, e.g., via phase or frequency modulation, to be used as the clock signal. In an alternative embodiment, a conventional transceiver may be included in the telemetry processor 18 to implement a radio frequency (RF) link which directly outputs received data bits on a dedicated pin. The transceiver may be, for example, a nRF2401A transceiver that is commercially available from Nordic Semiconductor, although other transceiver circuits may alternatively be used. The RF link does not follow the BlueTooth® standard, however, and therefore does not support two simultaneous communication channels. Additional circuitry is thus required to convert the audio signal into a suitable clock signal. Those skilled in the art will be aware of conventional circuitry that can be used to convert the audio signal into a suitable clock signal and to synchronize the clock signal with the data bits on the RF link.

Figure 8:
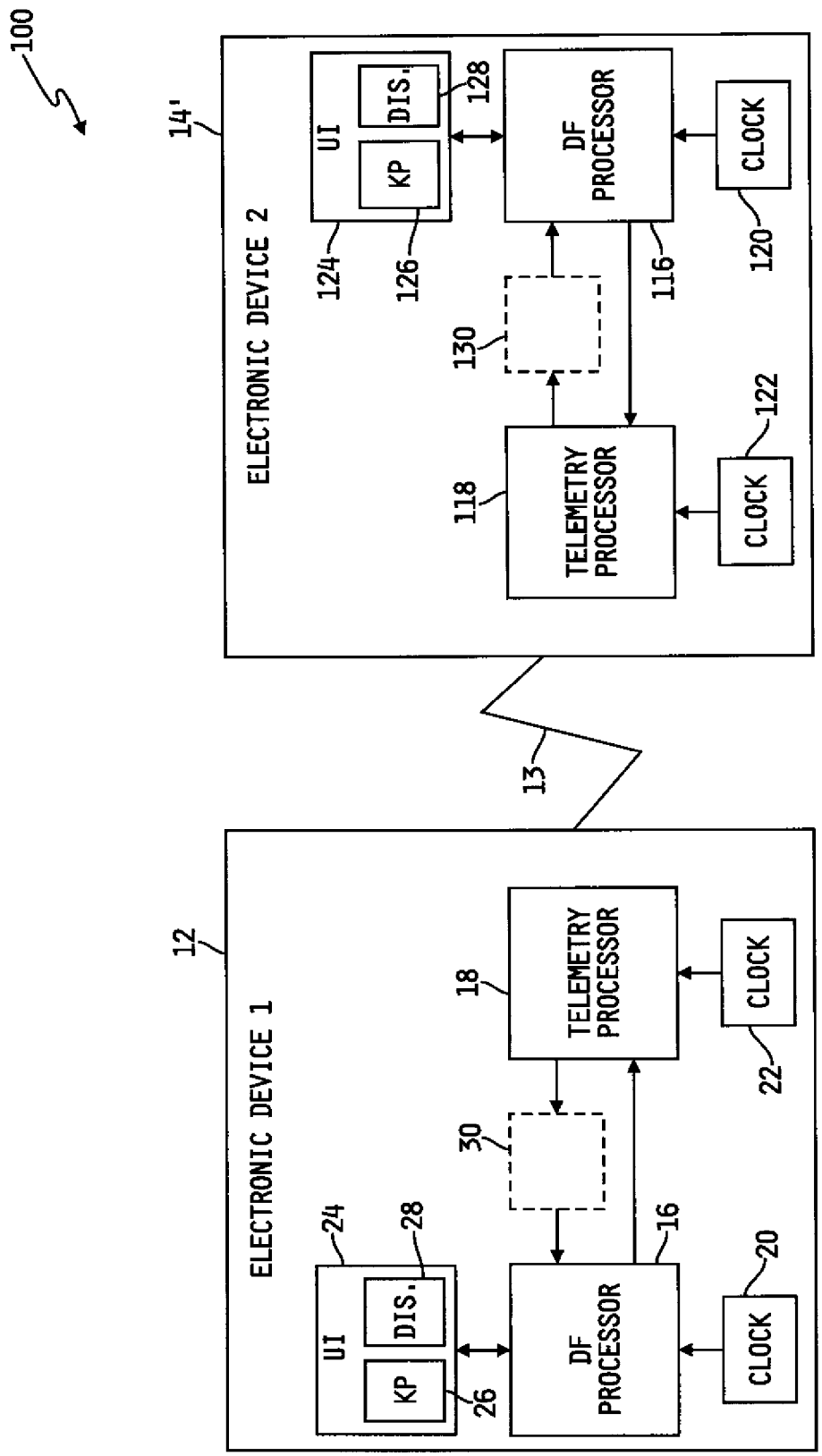
FIG. 8 is a diagram of yet another illustrative embodiment of a wireless communication system configured for wireless data and clock communications between two separate electronic devices.

Referring to FIG. 8, another illustrative embodiment of wireless communication system 100 is shown. As with the communication system 10 illustrated in FIG. 1, the wireless communication system 100 illustrated in FIG. 8 is configured for wireless communications between two separate electronic devices 12 and 14'. In this example, the electronic device 12 is a medical device and the electronic device 14' is a remote electronic device, although the electronic device 12 may alternatively be a wireless communication device and the electronic device 14' may be a medical device or the electronic devices 12 and 14' may both be medical devices or wireless communication devices.

In the illustrated embodiment, the electronic device 12 may be identical to the electronic device 12 illustrated and described with respect to FIG. 1, with the exception that the device function processor 16 is directly connected to the telemetry processor 18, and in this embodiment the device function processor 16 may provide information to the telemetry system 18 for wireless transmission to the electronic device 14'. It will be understood, however, that apart from the processors 16, 18 and the clock and data decoding circuit 30 the electronic device 12 may alternatively include more or fewer electronic components than that illustrated and describe with respect to FIG. 1. The electronic device 14' illustratively contains the same elements as the electronic device 12 with the same functions as the electronic device 12. Thus, for example, the electronic device 14' illustratively includes a device function processor 116 that is configured to control all functional operations of the device 14' but not including telemetry operations, i.e., wireless communications with the electronic device 12, a clock circuit, 120 electrically connected to the device function processor 116, wherein the timing of operation of the device function processor 116 is controlled by the clock circuit 120. The electronic device 14' further includes a telemetry processor 118 that is electrically coupled to the device function processor 116 via a clock and data decoding circuit 130 and also via direct electrical connection. The telemetry processor 118 is configured to control wireless communication with the electronic device 12, but not device functions, i.e., non-telemetry operations of the electronic device 14'. Another clock circuit 122 is electrically connected to the telemetry processor 118, and the timing of operation of the telemetry processor 118 is controlled by the clock circuit 122. In the illustrated embodiment the clock and data decoding circuit 130 connected between the device function processor 116 and the telemetry processor 118 may be implemented in any of the forms illustrated and described herein with respect to FIGS. 2-7. The electronic device 14' may further includes a user interface 124 that may include a keypad 126 and/or a display device 128 as illustrated and described with respect to FIG. 1

It should be understood that the embodiment illustrated in FIG. 8 is not limited to two identical electronic devices. It should also be understood that the two clock and data decoding circuits 30 and 130 need not be implemented identically, and either of the clock and data decoding circuits 30 and 130 may be implemented accordingly to any of the previous embodiments illustrated and described with respect to FIGS. 2-7.

In the embodiment of the system 100 illustrated in FIG. 8, the electronic devices 12 and 14' are each configured for two-way communications. The direct connection between the device function processor 16, 160 and the telemetry processor 30, 130 is used for transmitting data from the device function processor 16, 116 to the other device function processor 116, 16 in the form of wireless messages containing self-clocking codes. It should be clear to those skilled in the art that the communication system 100, according to the flow chart in FIG. 3, allows for bi-directional communication between the electronic device 12 and the electronic device 14'.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected.

What is claimed is:

1. An electronic device for processing information wirelessly received from another electronic device, the wirelessly received information including embedded data and clock information, the electronic device comprising:
   a first processor configured to extract at least one information packet containing the embedded data and clock information from the information wirelessly received by the electronic device from the another electronic device and to produce the at least one information packet at an output thereof,
   a clock and data decoding circuit having an input connected to the output of the first processor and an output, the clock and decoding circuit configured to extract the clock information from the at least one information packet, to fully decode the data from the at least one information packet, and to produce the fully decoded data and a clock signal corresponding to the extracted clock information at the output thereof, and
   a second processor having an input connected to the output of the clock and data decoding circuit, the second processor configured to synchronously read the fully decoded data received from the clock and data decoding circuit using the clock signal received from the clock and data decoding circuit, and to thereafter process the fully decoded data.

2. The electronic device of claim 1 wherein the output of the clock and data decoding circuit comprises a first output connected to the input of the second processor and a second output, separate from the first output, connected to the input of the second processor, and wherein the clock and data decoding circuit comprises:
   a phase lock loop circuit having an input coupled to the output of the first processor, a first output defining the first output of the clock and data decoding circuit and a second output, the phase lock loop circuit configured to extract the clock information from the at least one information packet and produce the clock signal at the first output thereof, and
   a decoder circuit having a first input connected to the output of the first processor, a second input connected to the second output of the phase lock loop circuit and an output defining the second output of the clock and data decoding circuit, the decoder circuit configured to fully decode the data from the at least one information packet and produce the fully decoded data at the output thereof.

3. The electronic device of claim 2 wherein the phase lock loop circuit is configured to produce a phase lock loop clock signal at the second output thereof,
   and wherein the decoder circuit is configured to fully decode the data in the at least one information packet using the phase lock loop clock signal.

4. The electronic device of claim 3 wherein the information wirelessly received by the electronic device from the another electronic device further comprises a preamble that precedes the at least one information packet,
   and wherein the first processor is configured to extract the preamble from the information wirelessly received by the electronic device from the another electronic device and to produce the extracted preamble at the output thereof,
   and wherein the phase lock loop circuit is configured to be responsive to the preamble to lock and run at a phase lock loop clock rate determined by information in the preamble, and to produce the phase lock loop clock signal at the phase lock loop clock rate.

5. The electronic device of claim 4 wherein the decoder circuit is configured to fully decode the data in the at least one information packet by removing the clock information from the at least one information packet as a function of the phase lock loop clock signal.

6. The electronic device of claim 4 wherein the phase lock loop circuit is configured to be responsive to transitions in values of the data contained in the at least one information packet to update the phase lock loop clock rate.

7. The electronic device of claim 1 wherein the information wirelessly received by the first processor from the another electronic device is received by the first processor in two separate channels in which a first channel contains the data and a second channel contains the clock information, and wherein the clock and data decoding circuit comprises means for processing the first channel to fully decode the data and means for processing the second channel to extract the clock signal from the clock information.

8. The electronic device of claim 7 in which the first channel is a data channel and in which the second channel is an audio channel.

9. The electronic device of claim 1 wherein the first processor is configured to wirelessly receive information from the another electronic device according to a predefined communication protocol, and wherein the first processor is configured to extract the at least one information packet from the information wirelessly received by the electronic device from the another electronic device according to the predefined communication protocol.

10. The electronic device of claim 1 wherein the information wirelessly received by the electronic device from the another electronic device is received as a wireless signal comprising self clocking codes in which the data and the clock information are combined into the wireless signal.

11. The electronic device of claim 3 wherein the information wirelessly received by the electronic device from the another electronic device further comprises a preamble that precedes the at least one information packet, and wherein the first processor is configured to extract the preamble from the information wirelessly received by the electronic device from the another electronic device and to produce the extracted preamble at the output thereof, and wherein the phase lock loop circuit is normally in a sleep state and is configured to be responsive to the preamble to wake up from the sleep state and to lock and run with a phase lock loop clock that operates at a phase lock loop clock rate defined by information contained in the preamble.

* * * * *